United States Patent [19]

Thariani et al.

[11] Patent Number: 5,577,997
[45] Date of Patent: Nov. 26, 1996

[54] FOOT AND BODY MAINTENANCE MASSAGE AND SCRUBBING TOOL

[76] Inventors: Kumail Thariani; Ann Thariani, both of 920 S. 58th St., Omaha, Nebr. 68106

[21] Appl. No.: 429,673

[22] Filed: Apr. 27, 1995

[51] Int. Cl.[6] ................................................. A61H 7/00
[52] U.S. Cl. ................................................ 601/135; 601/137
[58] Field of Search ................................ 601/136, 137, 601/138, 134, 135; 132/76.4

[56] References Cited

U.S. PATENT DOCUMENTS

| | | | |
|---|---|---|---|
| D. 99,352 | 4/1936 | Grapp | D4/136 |
| D. 203,793 | 2/1966 | Leopoldi | 132/76.4 |
| D. 285,131 | 8/1986 | Wilkeson | D30/40 |
| D. 304,265 | 10/1989 | Boweter | D4/136 |
| D. 324,778 | 3/1992 | Whittington | D4/136 |
| D. 343,476 | 1/1994 | Tomsick | D28/63 |
| D. 345,627 | 3/1994 | Thariani | D28/137 |
| 652,189 | 6/1900 | Littlejohn | 601/137 |
| 720,847 | 2/1903 | Sanford | 601/137 |
| 781,555 | 1/1905 | Schanz | 601/137 |
| 799,895 | 9/1905 | Doughty et al. | 601/137 |
| 904,800 | 11/1908 | Nelson | 601/137 |
| 1,006,630 | 10/1911 | Clarke | 601/137 |
| 1,382,436 | 6/1921 | Malm | 601/137 |
| 1,707,879 | 4/1929 | Schwartzman | 132/76.4 |
| 1,817,585 | 8/1931 | Samuel | 601/137 |
| 1,925,019 | 8/1933 | Wilson | 15/188 |
| 1,954,940 | 4/1934 | Mikel | 4/184 |
| 2,466,470 | 4/1949 | Norris | 272/57 |
| 2,806,470 | 9/1957 | Ferrier | 128/60 |
| 3,545,434 | 12/1970 | Woodruff | 601/137 |
| 4,461,285 | 7/1984 | Courtin | 601/137 |
| 4,813,405 | 3/1989 | Filip | 128/60 |
| 5,382,222 | 1/1995 | Yin-Jong | 601/135 |

FOREIGN PATENT DOCUMENTS

| | | | |
|---|---|---|---|
| 636160 | 1/1928 | France | 601/137 |
| 18840 | 8/1912 | United Kingdom | 601/135 |

*Primary Examiner*—Robert A. Hafer
*Assistant Examiner*—Brian E. Hanlon
*Attorney, Agent, or Firm*—Law Office of John A. Beehner

[57] ABSTRACT

A dual purpose massage and foot and body maintenance device for imparting a massaging action to the body and for removing dry skin and calluses from the feet and body. The tool has top and bottom surfaces and a peripheral wall extending circumferentially therearound. The peripheral wall is inclined downwardly and outwardly from the top surface and provides a gripping surface for holding the tool. The top surface being adapted for the massaging function and the bottom surface adapted for the foot and body maintenance function. The top surface has a plurality of generally hemispherically shaped protrusions adapted to contact and massage the body. The bottom surface performs the foot and body maintenance function. A plurality of depressions and riser portions or grooves is formed in the bottom surface of the tool. These grooves may be used to remove dry skin and calluses from the feet and body by rubbing the bottom of the tool against the dry skin and calluses.

10 Claims, 2 Drawing Sheets

5,577,997

FOOT AND BODY MAINTENANCE MASSAGE AND SCRUBBING TOOL

BACKGROUND OF THE INVENTION

1. Technical Field

The apparatus of the present invention relates generally to a body maintenance apparatus. More specifically, it relates to a dual purpose apparatus for providing both a means of massaging the body as well as a means for removing dry skin and calluses from the bottom of the feet, and the body.

Currently, no dual purpose devices such as that disclosed by the present invention exist providing an apparatus for both removing dry skin and calluses and body massage as well as providing additional mechanical advantages increasing the efficiency of the tool.

2. Description of the Prior Art

As mentioned, current prior art devices are generally limited to unitary purpose devices which provide either a massage function or foot maintenance function but not both. Furthermore, even considered separately, neither device as it exists in the prior art has the advantages shown by the present invention.

Prior art devices for removing dry skin and calluses from the bottom of the feet and body generally consist of an elongated, generally flat body having a rough surface thereon. This rough surface is placed in rubbing contact with the dry skin and calluses on the bottom of the feet and body. The device is grasped by hand and a rubbing motion generated against the dry skin and calluses with the rough surface of the device. This repetitive frictional contact between the rough surface of the device and the dry skin and calluses eventually causes the dry skin and calluses to be worn down and removed. One drawback of such prior art devices is the lack of an effective means of grasping the device. Consequently, there is a great need for a dual purpose foot maintenance massage and scrubbing tool which is capable of scrubbing the bottom of the feet and body as well as providing a massage of an afflicted area and which has a means for facilitating the mechanical motion necessary to remove the dry skin and calluses.

Therefore, it is a primary objective of the present invention to provide an apparatus having both a massage and foot and body maintenance capabilities.

It is a further objective of the present invention to provide an apparatus which has as part of its design a means facilitating the grasping thereof.

It is a further objective of the present invention to provide an apparatus taking mechanical advantage of this grasping motion, facilitating the application of pressure and rubbing of dry skin and calluses.

A further objective of the present invention is to provide an apparatus which has a bottom surface which is adapted to conform to the general shape of the bottom of a foot, and the curved surfaces of the body.

A further objective is to provide an apparatus having an appropriately lengthen securement member for releasably securing the device to the wrist of the individual using it.

A further objective is to provide an apparatus which may be used as a promotional item for beauty salons and the like.

A final objective is to provide an apparatus which has a sufficient thickness so as to avoid biting into the skin and having a smooth surface which is soft to the skin.

SUMMARY OF THE INVENTION

A dual purpose massage, foot and body maintenance device for imparting a massaging action to the body and for removing dry skin and calluses from the feet and the body. The tool has a top and bottom surfaces and a peripheral wall extending circumferentially therearound. The peripheral wall is inclined downwardly and outwardly from the top surface and provides a gripping surface for holding the tool. The top surface being adapted for the massaging function and the bottom surface adapted for the foot and body maintenance function. The top surface has a plurality of generally hemispherically shaped protrusions adapted to contact and massage the body. The bottom surface performs the foot and body maintenance function. A plurality of depressions and riser portions or grooves is formed in the bottom surface of the tool. These grooves may be used to remove dry skin and calluses from the feet and the body by rubbing the bottom of the tool against the dry skin and calluses.

DESCRIPTION OF THE PREFERRED EMBODIMENT

The foot maintenance massage and scrubbing tool of the present invention is a dual function apparatus. The two primary functions served by the present invention are the massaging function and the foot maintenance function. These two functions are provided by the top 20 and bottom 30 portions, respectively, of the tool of the present invention.

Figure 3:
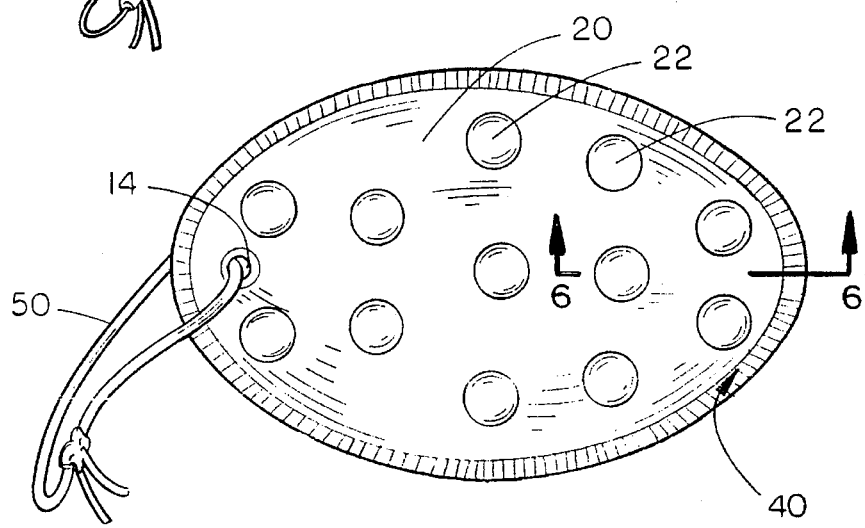
FIG. 3 is a top view of the foot maintenance apparatus of the present invention.

The massaging function is provided by a plurality of hemispherically shaped protrusions 22 on the top surface 20 of the tool apparatus 10. These hemispherical protrusions 22 are, in the preferred embodiment, adapted to be arranged on the top surface 20 in approximately the same position as would be the fingers of a masseuse (FIG. 3). Therefore, the top surface 20 of the maintenance tool 10 is adapted to simulate a massage.

The foot maintenance function of the apparatus 10 is provided by a series of depressions and riser portions or grooves 32 and 34, arranged on the bottom surface 30 of the maintenance tool 10. The foot maintenance function is accomplished by the frictional force of rubbing the rough underside of the maintenance tool across the bottom of the foot. These functions and features of the tool 10 are described in more detail below in conjunction with the individual figures.

Figure 1:
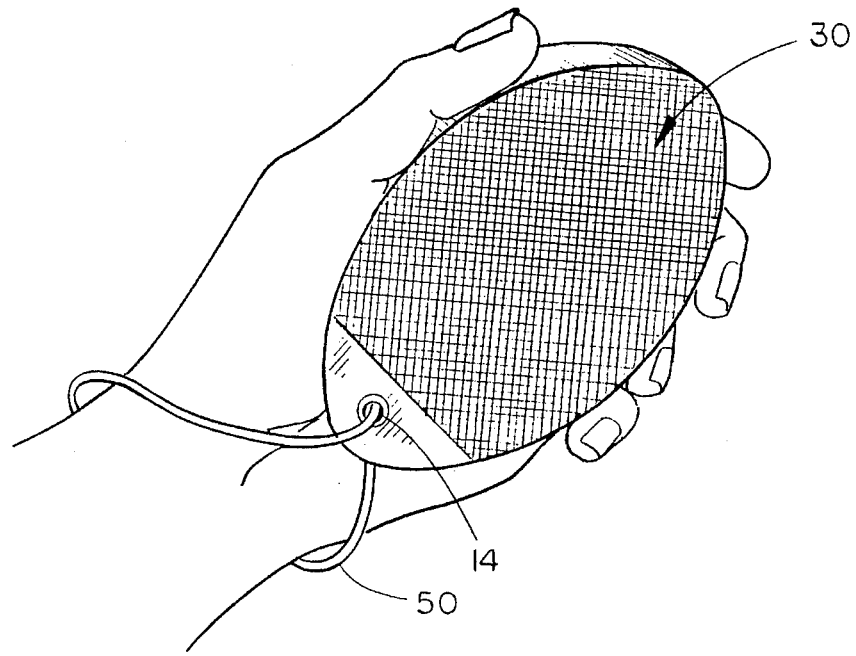
FIG. 1 is a bottom perspective view of the foot maintenance massage and scrubbing tool apparatus of the present invention.

FIG. 1 is a bottom perspective view of the maintenance tool 10 of the present invention. As mentioned above, the bottom portion 30 of the maintenance tool is operative to effect the foot and body maintenance function of the apparatus. In the present invention, it is anticipated that this foot and body maintenance function will consist primarily of the removal of dry skin and calluses from the bottom of the feet and the rest of the body. This removal is effectuated by the repetitive frictional rubbing of the dry skin and calluses on the foot with the rough surface provided by the bottom 30 of the tool 10. In the present invention, this rough surface is formed by a series of depression and riser portions "cut" into the bottom 30 of the maintenance tool 10. In the present invention, these depression and riser portions are formed by a series of grooves 32, 34 (FIG. 5) in the bottom surface 30 of the maintenance tool 10. The grooves are preferably arranged in two series of parallel lines. The first series 32 is inclined at an approximately 45° angle to the longitudinal axis of the maintenance tool 10. Another series of parallel grooves 34 is oriented at approximately a 90° angle to the first set of parallel grooves. Thus, the two series of grooves 32, 34 form a "criss-cross" pattern on the bottom surface 30 of the tool 10. This "criss-cross" pattern of grooves comprises the rough surface which is placed in rubbing contact with the bottom sole of the foot and, which when rubbed against the dry skin and calluses, is operative to remove them from the bottom of the feet, and the rest of the body.

As indicated in FIG. 1, the maintenance tool 10 is adapted to be grasped on the side thereof. In order to facilitate this grasping of the maintenance too, a wall 40 extends circumferentially around the maintenance tool 10. As seen in FIG. 1, the individual using the maintenance tool 10 would grasp the wall 40 with the hands, exposing the bottom surface 30 thereof for placement adjacent the bottom surface of the sole of the foot and the rest of the body. Additional details of the wall 40 and the hemispherical protrusions 22 are shown in the side view of FIG. 2.

Figure 2:
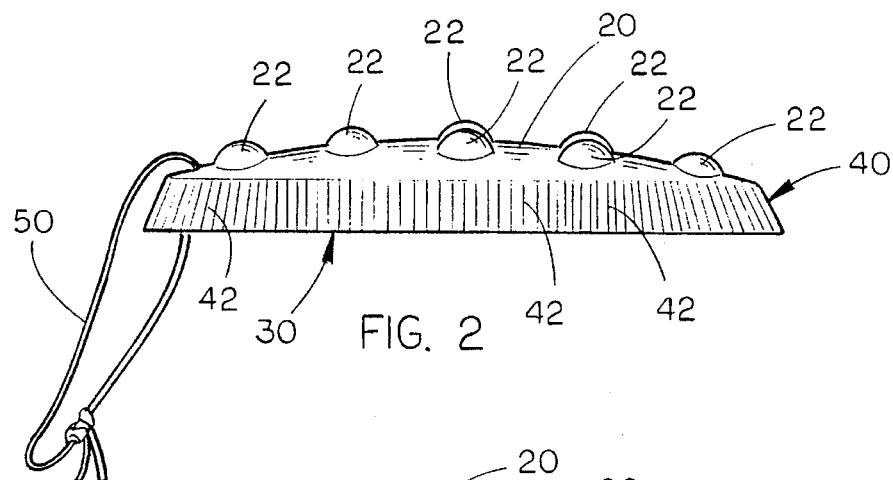
FIG. 2 is a side view of the foot maintenance tool of the present invention.

The side view of FIG. 2 illustrates in better detail the design of wall 40 which circumferentially surrounds the maintenance tool 10. Also shown in this figure are the plurality of hemispherical protrusions 22 projecting from the top surface 20 of the maintenance tool 10. As discussed above and shown in more detail in later figures, these hemispherical protrusions 22 are arranged in a pattern on the top surface 20 of the maintenance tool 10 to simulate the approximate placement of the finger tips of a hand as they would be placed adjacent the massaged body portion. As seen in FIG. 2, these hemispherically shaped protrusions 22 are placed on the top surface 20 of the maintenance tool 10. As also seen in this figure, wall 40 is inclined at approximately a 45° angle. This inclination facilitates the grasping of the tool 10 by the hand. Additionally, a gripping surface is provided by a plurality of vertically oriented ridges 42 placed circumferentially surrounding the wall 40. This plurality of ridges 42 in wall 40 further serves to facilitate the frictional grasping and engagement of the tool 20 with the hand.

Also illustrated in the figures is the connection means 50. In the preferred embodiment, connection means 50 may be a single piece of rope, twine or the like which is looped through hole 14 in rear portion of tool 10. The connection means 50 is of a length which allows the hand to be inserted therethrough. The length of connection means 50 also allows the tool 10 to be grasped by the hand in a working position as shown in FIG. 1. Connection means 50 is short enough, however, that when the tool 10 is held in the working position indicated in FIG. 1, a minimum amount of slack exists in connection means 50. Thus, if the user were to lose his or her grip on the tool 10, it would fall a minimum distance.

FIG. 3 shows with particular clarity the positioning of the generally hemispherical protrusions 22 on the top surface 20 of the maintenance tool 10. As mentioned above, these hemispherical protrusions 22 are preferably placed in a position on top surface 20 simulating the approximate positioning of the finger tips. Also indicated in FIG. 3 is the inward inclination of wall 40 at top surface 20 of the maintenance tool 10.

Figure 4:
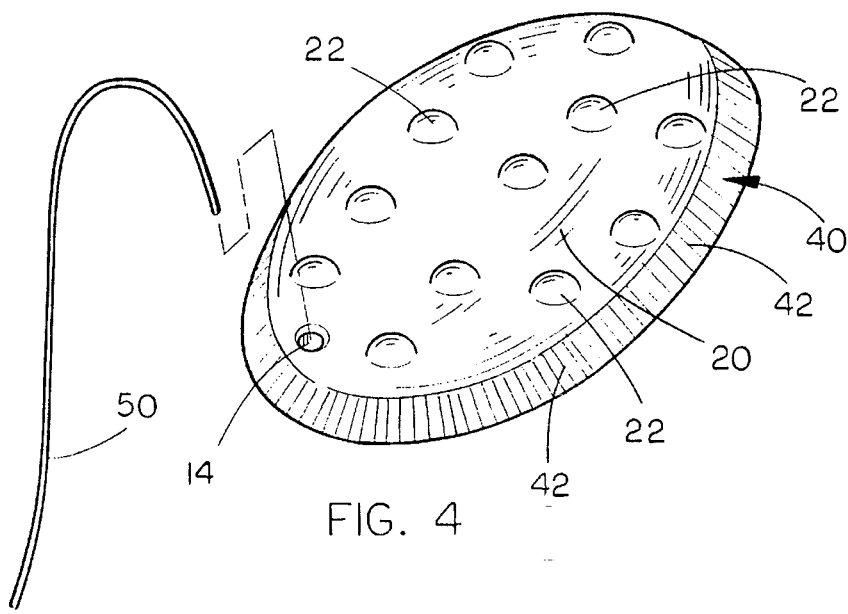
FIG. 4 is top a perspective view of the foot maintenance apparatus showing how the wrist-connecting strap is used in conjunction therewith.

FIG. 4 is a top perspective view of the maintenance tool 10 showing the hole 14 in tool 10 for receiving connection means 50. As mentioned above, connection means 50 in the present invention would preferably be a single piece of rope or the like which would have the ends thereof tied together, forming a closed loop. FIG. 4 also shows the inward inclination of the wall 40 at the top surface 20 of the maintenance tool 10.

Figure 5:
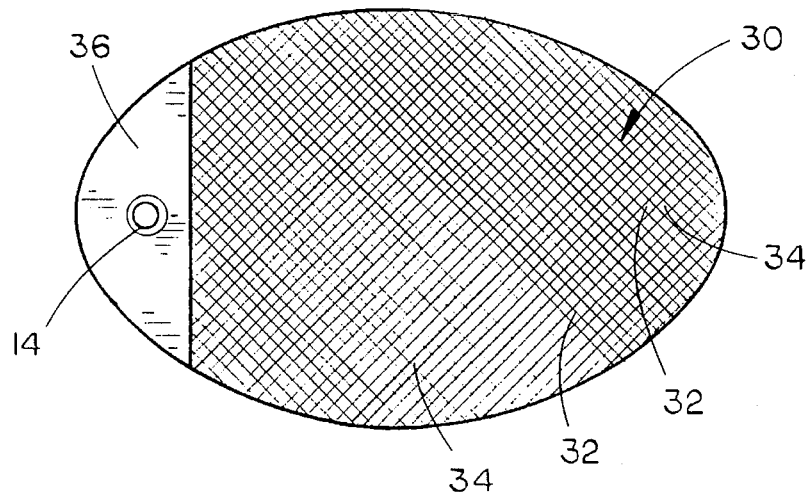
FIG. 5 is a bottom view of the foot maintenance apparatus showing the dry skin and calluses-removing protrusions on the bottom thereof.

FIG. 5 is a bottom view of the maintenance tool showing the plurality of depression and riser portions, or grooves, 32 and 34, formed in the bottom surface 30 adapted to accomplish the foot and body maintenance function of the apparatus. As mentioned above, the maintenance function of the apparatus primarily comprises removal of dry skin and calluses from the bottom of the feet and the rest of the body. In the preferred embodiment, this foot and body maintenance is accomplished by the continuous and repetitive rubbing and frictional engagement of the foot bottom and the rest of the body with a rough surface. This rough surface in the preferred embodiment is the aforementioned plurality of depressions and risers, or grooves, 32 and 34 in the bottom surface 30 of the maintenance tool 10. As mentioned above, the preferred pattern for this plurality of depression and riser portions comprises a series of grooves 32 running in one direction at essentially a 45° angle to the longitudinal axis of the maintenance tool. A second series of grooves 34 is cut at a 90° angle to the original set. Thus, the "criss-cross" pattern, illustrated in FIG. 5, is formed in the bottom 30 of the maintenance tool 10. Clearly other patterns are possible although the "criss-cross" pattern is believed to be the most efficient.

Figure 6:
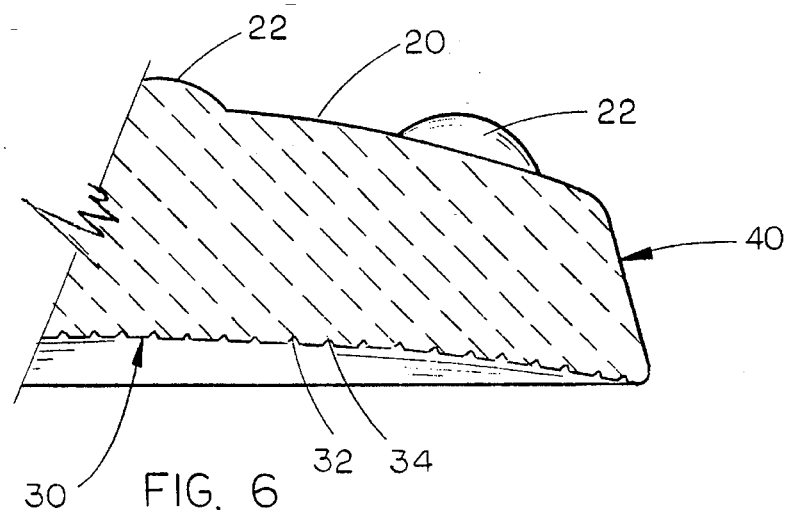
FIG. 6 is a cross-sectional view taken along the lines indicated in FIG. 3 showing in particular detail the hemispherical massaging protrusions from the top thereof and the dry skin and calluses-removing depressions and riser portions on the bottom surface thereof.

FIG. 6 is a cross-sectional view taken along the lines indicated in FIG. 3 above. FIG. 6 illustrates with particular clarity the slight concave nature of the bottom 30 of the maintenance tool 10. Additionally, FIG. 6 illustrates the integral formation of the hemispherical protrusions 22 in the top surface 20 of the tool 10. As illustrated clearly in the figure, the plurality of grooves 32 and 34 are cut in this bottom concave surface 30. As mentioned above, the purpose for the concave shape of this bottom surface 30 is so that it will more closely adapt to the shape of the bottom of the foot and the curves of the body maximizing the pressure applied thereto.

As mentioned above and indicated in the figures, the preferred overall shape of the maintenance tool 10 is generally oval, allowing the maintenance tool 10 to fit comfortably in a hand.

As mentioned above, the positioning and spacing of the hemispherical protrusions 22 on the top surface 20 of the maintenance tool 10 are designed to perform the massage function of the tool 10. There are two opposing considerations when determining the height of protrusions 22. First, they should not be so high that they are felt individually.

Rather, they should be felt as part of a network. Conversely, if they are too shallow, they will not properly massage the muscles. The height of the hemispherical protrusions in the preferred embodiment are approximately ½ inch or approximately ¼ the thickness of the body. This depth prevents the hemispherical protrusions being sensed individually but rather allows the overall sensation of a masseuse to be achieved. Obviously this height is not a precise requirement. Rather, it is simply believed that the height permits the desired effect.

The curved nature of the bottom surface 30 of the maintenance tool 10 permits better surface contact with the bottom sole of the foot and the curved surfaces of the body. Additionally, this curved surface 30 reduces the amount of wrist movement necessary to impart the frictional rubbing due to the natural curving movement provided thereby. Still further, this concave surface facilitates application of the amount of pressure which may be applied by this natural gripping of the tool. Conversely, the convex shape of the top surface 20 of the maintenance tool 10 facilitates a natural curved movement with even pressure at the contact points with hemispherical protrusions 22. The hemispherical protrusions 22 are of a sufficient diameter that any contact with any sharp corners of the maintenance tool, such as at the junction of the top surface 20 and wall 40, is avoided. As mentioned, the maintenance tool 10 comprises an ergonomic design adapted to fit the hand for gripping thereof.

One possible use embodiment of the apparatus is that it may be used when wet such as with the application of oils to the skin or when it is used in the shower. The design of the hemispherical protrusions on the top surface, and the grooves cut in the bottom surface 30, allow for better airflow and drying of the tool, even when placed on a flat surface. With the unique design of the maintenance tool apparatus 10, the water drips downwardly and away, allowing the airflow surrounding the tool to dry it.

In addition to the removal of dry skin and calluses from the underside of the foot and body, the maintenance tool 10 may also be used for cleaning of the foot. One example of this use embodiment is to clean grass stains from the underside of the foot. Of course, the use of the maintenance tool 10 is not limited to the underside of the feet, but rather may be used wherever contact with the ground is made, such as on the heels, soles, tips of the toes, knees, etc., or wherever dry skin and calluses occurs on the body.

In the preferred embodiment, the edges formed by the joining of the wall 40, top surface 20, and bottom surface 30, respectively, would be tapered slightly so as to avoid any sharp edges at the junctions thereof. As mentioned above, the wall 40 comprises a series of generally vertically oriented grooves 42 placed circumferentially therearound to facilitate the gripping of the maintenance tool 10. This feature is of great utility when the maintenance tool is utilized in a wet configuration, wherein oil may be first applied to the skin. In this situation, obviously the oil will be transmitted to the surface of the maintenance tool itself, causing it to become slippery. Alternatively, the maintenance tool may be utilized in the shower or the like wherein soap and water may be transmitted against the surface of the maintenance tool, causing it to become quite slippery. In either case, the plurality of vertical ridges 42 in the wall 40 allows a tight, secure grip to be placed on the maintenance tool regardless of the use environment.

In the preferred embodiment, the maintenance tool 10 may be constructed of a terra cotta material. This material has several qualities which make it well suited for use in fabricating the maintenance tool. For example, another use envisioned with the present invention is to warm the apparatus prior to use. The terra cotta material is adapted to hold heat for an extended period. The heat can then be radiated through the hemispherical protrusions in the top surface 20 during use. Obviously, there are many methods of heating the tool. For example, the maintenance tool 10 may be heated in the microwave for approximately 30 seconds or perhaps in warm water or even by the sun prior to use. This ability to hold heat presents a unique advantage of the present invention over prior art devices. Another benefit to use of the preferred terra cotta material is the resistance to absorbing moisture due to its density and its disability and lack of decomposition, due to its becoming "vitrified" during its manufacture. Thus, it is well suited for use in the aforementioned uses with soap and water or body oils.

The preferred method of fabricating the maintenance tool 10 is to stamp out individual units using the RAM press, as opposed to pouring. This press method generates intense pressure in forming the maintenance tool which causes the terra-cotta to be extremely dense. Immediately after stamping the individual units, they may be removed from the mold. Unlike pouring with a plaster of Paris mold, there is no need to wait for any extended time for drying. Other fabrication methods may also be suitable.

Another benefit of the density of terra cotta material is that it may be easily sanitized or sterilized using either a liquid treatment or through heat or chemical treatments. The sterilization is facilitated by the design of the maintenance tool which inhibits the harboring of any bacteria thereon and encourages quick drying. For use in the professional environment, the maintenance tool may be sanitized by placing it in a sanitizing liquid for some period of time, perhaps 20 minutes between patients.

As mentioned above, the maintenance tool 10 is adapted to receive a connection means 50 facilitating the handling thereof. In the preferred embodiment, this connection means 50 is a single strand of ropes which has its ends tied together to form a closed loop. As also mentioned, in designing a connection means, the length thereof is an important consideration. It is necessary, of course, that the length be sufficient so that a person can get his or her hand therethrough. Conversely, it is important that the length not be too great such that if the grip on the maintenance tool is lost, the connection means is engaged prior to its falling to the floor or onto the foot. Another consideration for connection means 50 is that it be sufficiently thick so as to not cut into the skin when the means is engaged. Another purpose for the connection means 50 is that it be sufficiently thick so as to not cut into the skin when the means is engaged. Another purpose for the connection means 50 is to provide a mechanism whereby the maintenance tool 10 may be hung on a post for drying. Additionally, from a marketing standpoint,t he maintenance tools may be displayed for sale by hanging them on a post using the connection means 50.

Another possible use of the apparatus is in an environment referred to as "aroma therapy". In this situation,t he fragrance oil may be placed on some of the hemispherical protrusions 22 wherein heat or friction would cause the aroma to be released from the protrusions 22. As is well understood in the art, the fragrance oil is generally not placed directly on the skin due to its concentration, and expense, and risk of skin irritation. Rather, it is desirable to place a small amount of the fragrance oil on an object and then transmit it indirectly to skin already moistened with massage oil or soap and water.

Obviously, the maintenance tool may be fabricated using many different colors. As will be understood in the art, if the maintenance tool is to be utilized for massage therapy, it may be desirable to fabricate the maintenance tool out of a dark color so that application of the oil to the maintenance tool will not cause it to look dirty or stained. Additionally, fabrication of the maintenance tool using the terra cotta material allows the maintenance tool to be cleaned with soap and water.

As mentioned above, the sloping nature of sidewall 40, illustrated best in FIGS. 2 and 6, facilitates the application of downward pressure which is especially helpful in the foot-scrubbing use embodiment. This sloping wall 40 also prevents the fingers from overlaying the scrubbing area which might occur if a straight side were used. Conversely, when the maintenance tool 10 is flipped over for use of the massage function, it is not a concern that the hand may overlap some of the surface since the hemispherical protrusions 22 already establish a contact with the body surface.

Cleaning of the maintenance tool is greatly facilitated by the fact that the surface of the maintenance tool 10 on and around the hemispherical protrusions is very smooth and lacking any grooves or the like. Consequently, oil is not retained in the surface and may be easily cleaned off. In the preferred embodiment, the maintenance tool would be constructed of a thickness sufficient to comfortably fit in the hand. This thickness, in addition to the comfort factor, facilitates the absorption and storage of heat therein for use in heated treatments as discussed above. It will finally be noted that there is a relatively flat surface 36 on the underside of the apparatus as illustrated in FIGS. 1 and 5. This flat surface may be used for display of name or other logo or the like.

It is obvious that numerous other modifications and variations of the present invention are possible in view of the above teaching. For example, the size, shape and construction material may all be altered. Additionally, different groove patterns on the underside of the tool may be utilized. Still further, the size and height of the hemispherical protrusions may be altered.

Therefore, it is to be understood that the above description is in no way intended to limit the scope of protection of the claims and the representative only of the several possible embodiments of the present invention.

There has thus been shown and described an invention which accomplishes at least all of the stated objectives.

I claim:

1. A dual purpose massage and foot and body maintenance device for imparting a massaging action to the body of a person and for removing dry skin and calluses from the feet and body comprising:

a scrubber body having generally convex top and generally concave bottom surfaces and a peripheral wall extending circumferentially therearound, said peripheral wall being inclined downwardly and outwardly from said top surface to said bottom surface, said wall providing a gripping surface by which said scrubber body may be held for manually moving said top and bottom scrubber body surfaces across said body of a person, said top surface being adapted for said massaging action and said bottom surface adapted for foot and body maintenance, said scrubber body being comprised of a solid, vitrified, terra cotta material and further having, a plurality of generally hemispherically shaped protrusions on said top surface, said hemispherically shaped protrusions being adapted to contact and massage the body of a person when placed in rubbing contact therewith, and a plurality of depressions and riser portions comprising a series of grooves formed in said bottom surface and adapted to remove dry skin and calluses from the feet and body upon rubbing of said depressions and riser portions against said dry skin and calluses.

2. The dual purpose massage and foot and body maintenance device of claim 1 wherein said depression and riser portions comprise a first series of generally parallel grooves and a second series of generally parallel grooves rotated approximately ninety degrees to said first series of grooves.

3. The dual purpose massage and foot and body maintenance device of claim 1 wherein said top surface hemispherical protrusions are positioned throughout said top surface.

4. The dual purpose massage and foot and body maintenance device of claim 1 wherein said top surface hemispherical protrusions are positioned to correspond approximately with placement of the fingers of a human hand when giving a massage.

5. The dual purpose massage and foot and body maintenance device of claim 1 wherein said hemispherical protrusions are approximately ¼ the thickness of said scrubber body.

6. The dual purpose massage and foot and body maintenance device of claim 1 wherein said scrubber body is generally oval shape.

7. The dual purpose massage and foot and body maintenance device of claim 1 wherein said peripheral wall has a plurality of ribs therein facilitating the gripping thereof.

8. The dual purpose massage and foot and body maintenance device of claim 1 wherein said depressions and riser portions are arranged in a generally uniform distribution across an area of said bottom surface.

9. The dual purpose massage and foot and body maintenance device of claim 1 wherein the radius of said hemispherical protrusions is between ⅜ and 9/16".

10. The dual purpose massage and foot and body maintenance device of claim 1 wherein the radius of said hemispherical protrusions is approximately ½".

\* \* \* \* \*